(12) United States Patent
Horn

(10) Patent No.: US 7,618,805 B2
(45) Date of Patent: Nov. 17, 2009

(54) GAMMA-STERILISABLE NUTRIENT MEDIUM BASED ON CASEIN SOYA PEPTONE AGAR

(76) Inventor: Jürgen Horn, Kurt-Schumacher-Ring 83, Egelsbach (DE)

( * ) Notice: Subject to any disclaimer, the term of this patent is extended or adjusted under 35 U.S.C. 154(b) by 925 days.

(21) Appl. No.: 10/623,241

(22) Filed: Jul. 18, 2003

(65) Prior Publication Data

US 2004/0106186 A1 Jun. 3, 2004

(30) Foreign Application Priority Data

Jul. 23, 2002 (DE) .................................. 102 33 346

(51) Int. Cl.
*C12N 1/20* (2006.01)
(52) U.S. Cl. .................................................. 435/253.6
(58) Field of Classification Search ................ 435/253.6
See application file for complete search history.

(56) References Cited

U.S. PATENT DOCUMENTS

| 5,968,807 | A | * | 10/1999 | Kaiser | 435/253.6 |
| 6,136,554 | A | * | 10/2000 | Bochner | 435/34 |
| 6,908,745 | B2 | * | 6/2005 | Horn | 435/34 |

* cited by examiner

*Primary Examiner*—Jon Weber
*Assistant Examiner*—Kailash C. Srivastava
(74) *Attorney, Agent, or Firm*—Norris McLaughlin & Marcus, PA

(57) ABSTRACT

A gamma-sterilizable nutrient medium based on casein soya peptone agar for the detection of microorganisms in hydrogen peroxide-bearing air or on hydrogen peroxide-bearing surfaces, with a content of between 2 and 10% by weight of sodium thioglycolate, between 5 and 20% by weight of sodium thiosulfate and between 10 and 30% by weight of sodium disulfite in each case with respect to the agar. Preferably the agar used is microbial content test agar and the nutrient medium may contain between 0.1 and 0.25% by weight of sodium pyruvate with respect to the agar. If bromocresol purple and bromocresol violet are used as pH-indicators the nutrient medium may also contain polyvinylpyrrolidone.

23 Claims, No Drawings

GAMMA-STERILISABLE NUTRIENT MEDIUM BASED ON CASEIN SOYA PEPTONE AGAR

CROSS-REFERENCE TO RELATED APPLICATIONS

This application claims priority to Germany 10233346. 7 filed 23 Jul. 2002.

FIELD OF THE INVENTION

The invention relates to a gamma-sterilisable nutrient medium based on casein soya peptone agar for the detection of microorganisms in hydrogen peroxide-bearing air or on a hydrogen peroxide-bearing surface.

More particularly this can be used for the detection of microorganisms such as bacteria, yeasts and fungi.

BACKGROUND OF THE INVENTION

Hydrogen peroxide can be used for fumigating isolators or entire rooms in order to destroy microorganisms which are possibly to be found therein. The hydrogen peroxide in gas form condenses on the fumigated surfaces, as a between 30% and 35% saturated solution. Prior to the start of manufacturing procedures, quality control investigations in respect of sterility or other operations in the fumigated clean room areas, they are sterily ventilated, whereafter levels of concentration of between 0.3 and 6 ppm, in general below 1 ppm, of germs remain in the air. Investigations in regard to such air-borne germs which are possibly still present is effected with air-borne germ collecting devices operating on the basis of the impaction or rotation principle, with the germ-bearing particles being deposited on agar surfaces.

Surprisingly the small amounts of hydrogen peroxide vapors are concentrated in the course of collecting 1000 liters of air in casein soya peptone agar, in accordance with United States Pharmakopoeae, 8th Supplement, USP-NF, <1116>, 4426-4431, on concentrations of over 100 ppm in agar. Spores are already restrained by levels of hydrogen peroxide concentration of 10 ppm and vegetative cells and microorganisms are already restrained by an even more markedly lower concentration of hydrogen peroxide. That adversely affects to a considerable degree the detectability of microorganisms which are still present.

Normal agar media have a contamination rate of about 0.1%, that is to say 1 non-sterile unit among 1000, and therefore do not comply with the notion of sterility which allows only one non-sterile unit among $10^6$ (one million). As the media used for the investigatory procedure are employed to investigate clean rooms which were previously rendered germ-free by fumigation, it would be desirable for no germs to be introduced with the agar materials for testing for freedom from germs, and therefore the expectation is for sterile media.

For conducting detection procedures of the above-indicated kind, it is possible to use media such as the Baird-Parker medium (Journ. Applied Bacteriology 25:12, 1962, Baird-Parker) with 1% of sodium pyruvate, being a sodium salt of pyruvic acid or 2-oxopropionic acid, which inter alia are suitable for the isolation of *Staphylococcus aureus* after heat damage or storage of frozen or dried vegetative cells. The disadvantage of Baird-Parker agar is the low level of stability and durability of the finished agar medium.

The addition of catalase to this and other media for improving the growth of bacteria from the air is also known, in which respect reference may be made to Journ. Applied and Environmental Microbiology 57: 2775-2776, 1991, Balkumar Marthi. Catalase breaks down hydrogen peroxide into water and oxygen. Catalase however is inactivated at 55° C., which presupposes drawing off agar at markedly below 55° C. That however is scarcely a viable option because of gelling of the agar at temperatures around 50° C. In addition the oxygen resulting from the hydrogen peroxide causes bubbles and cracks in the agar, which causes extreme difficulty in detecting colonies which grow on the agar.

Also known is D/E-agar which neutralises a wide range of antiseptic and disinfecting chemicals including quaternary ammonium compounds, phenol, iodine and chlorine compounds, mercury (Merthiolate), formaldehyde and glutaraldehyde (Difco Handbook, D/E-Agar). That Difco Handbook does not describe neutralisation of hydrogen peroxide. The disadvantage of D/E-agar is the short durability life of the ready agar medium of only about two and a half months and the changes in the medium in the event of radiation doses of 16-25 kgray, which are necessary for reliable gamma-sterilisation.

In addition D/E-agar is not very stable in respect of pH and at a pH of 7.6±0.2, is already of a very high pH-value. Upon drifting towards even higher pH-values such as 8.0, namely only 0.2 above the upper limit of the range specified above, the situation already involves marked restraints in respect of germs to be detected.

SUMMARY OF THE INVENTION

An object of the present invention is to afford a gamma-sterilisable nutrient medium for the detection of microorganisms in hydrogen peroxide-bearing air or on hydrogen peroxide-bearing surfaces, which does not suffer from the above-indicated disadvantages and which affords enhanced operating results.

Another object of the present invention is to provide a gamma-sterilisable nutrient medium for the detection of microorganisms, which affords enhanced stability thereby facilitating storage and despatch and also providing a long potential period of use.

In accordance with the principles of the present invention the foregoing and other objects are now attained by a gamma-sterilisable nutrient medium based on casein soya peptone agar for the detection of microorganisms in hydrogen peroxide-bearing air or on a hydrogen peroxide-bearing surface, with the addition of between 2 and 10% by weight of sodium thioglycolate, between 5 and 20% by weight of sodium bisulfite and between 10 and 30% of sodium thiosulfate, in each case with respect to the agar. It was surprisingly found that agar medium based on casesin soya peptone agar neutralises hydrogen peroxide in levels of concentration as occur when collecting air-borne germs in isolators with hydrogen peroxide residual content, when the above-outlined additions are implemented.

Preferably the casein soya peptone agar employed is the Microbial Content Test Agar (MCT Agar; Difco 0553-07-4) which comprises casein soya peptone with the addition of sorbitan monooleate=Tween 80® and lethicin. Those media are also pH-stable by buffering in the pH-range of between 7.1 and 7.5.

Conventional buffering with phosphate buffer alone results in precipitation phenomena so that the medium has poor growth properties. As is known that can be avoided by buffering with MOPS (morpholinopropane sulfonic acid). MOPS however is very expensive. Surprisingly however it has now been found that partial replacement of phosphate by MOPS is possible without involving growth-reducing precipitation phenomena. Preferably, of the total amount of buffer between 20 and 50% is used in the form of MOPS, in which case MOPS is added firstly and thereafter the balance of between 50 and 80% of the total buffer content is slowly added, as phosphate buffer.

The pH-indicators which are usually added, bromocresol purple and bromothymol blue, are destroyed by gamma irradiation at between 16 and 25 kgray, with the consequence of the agar being of a gray appearance, which causes substantial difficulties in terms of evaluating white to gray colonies. It was surprisingly found that this can be prevented by the addition of polyvinylpyrrolidone in an amount of between 10 and 50%, preferably between 30 and 45%, with respect to the agar. The blue-violet to blue-green color is then maintained, which substantially facilitates evaluation of and checking for grown colonies.

Surprisingly, the hydrogen peroxide-neutralising action of the nutrient media according to the invention can be boosted by the addition of between 0.05 and 0.25% of pyruvate. These levels of concentration which are substantially lower in comparison with the Baird-Parker medium are of economic importance, because of the high price of sodium pyruvate.

Media according to the invention, buffered in the range of between pH 6.8 and 7.4, with the above-specified pH-indicators and the addition of sodium pyruvate and polyvinylpyrrolidone, are stable for 6 months, which substantially facilitates storage and shipping, and also guarantees that the customer has a long potential period of use. Those media are further capable of neutralising 2% $H_2O_2$-solutions which are applied directly and permitting subsequent growth of microorganisms. In comparison for example normal soya casein peptone agar no longer permits germ growth after exposure with only 0.02% hydrogen peroxide.

In addition, for better growth of germs which were damaged by drying out, for example in air or on a surface, it is possible to add betaine, glycine, cystine, proline and asparagine.

The Examples set out hereinafter further specifically illustrate the invention.

PREFERRED EMBODIMENTS

Example 1

Medium with Color Indicator for Applying to $H_2O_2$-bearing Surfaces

| | |
|---|---|
| Basic medium Microbial Content Test Agar (Difco 0553-07-4 = MCT Agar) | 23 g |
| Agar-agar (comprising casein soya peptone, common salt, lecithin, sorbitan-monooleate and agar) | 12 g |
| Polyvinylpyrrolidone (PVP 360) betaine (Sigma B3501)0.03 | 10 g |
| Betaine (Sigma B3501) | 0.03 g |
| L-glycine (Merck 104201) | 0.05 g |
| L-cystine (Merck 1028136) | 0.025 g |
| L-proline (Merck 107434) | 0.025 g |
| Pyruvic acid, Na-salt (Merck 106619) = sodium pyruvate | 0.25 g |
| L-asparagine (Merck 101565) | 0.025 g |
| Glucose (Merck 107074) | 2.5 g |
| Sodium thioglycolate (Sigma T0632) | 1.0 g |
| Sodium disulfite (Merck 106528) | 2.5 g |
| Sodium thiosulfate (Merck 106516) | 6.0 g |
| Bromocresol purple (Merck 103025) | 0.025 g |
| Bromothymol blue (Merck 103026) | 0.025 g |
| Aqua dest | ad 1 liter |
| Adjust pH to 7.3 ± 0.2, autoclave for 15 min at 121° C. and after cooling add in sterile filtered condition: | |
| Yeast extract (Marcor, 10 g yeast extract stirred cold into 100 ml VE-water and sterile-filtered) | 2.5 ml |

-continued

| | | |
|---|---|---|
| Phosphate buffer pH 7.3 | 1 molar solution | 20 ml |
| MOPS buffer pH 7.3 | 4 molar solution | 6 ml |
| (Sigma M1254, morpholinopropane sulfonic acid) (first add MOPS, thereafter phosphate slowly) | | |
| L-ascorbic acid (Na-salt Sigma A7631, 1 g in 2 ml VE-water | | 0.5 ml |

Example 2

Medium Without Color Indicator for the Detection of Air-borne Germs in $H_2O_2$-bearing Isolator Air

| | | |
|---|---|---|
| Basic medium Microbial Content Test Agar (Difco 0553-07-4) | | 23 g |
| Agar-agar | | 12 g |
| Betaine (Sigma B3501) | | 0.03 g |
| L-glycine (Merck 104201) | | 0.05 g |
| L-cystine (Merck 1028136) | | 0.025 g |
| L-proline (Merck 107434) | | 0.025 g |
| Pyruvic acid, Na-salt (Merck 106619) = sodium pyruvate | | 0.25 g |
| L-asparagine (Merck 101565) | | 0.025 g |
| Glucose (Merck 107074) | | 2.5 g |
| Sodium thioglycolate (Sigma T0632) | | 1.0 g |
| Sodium disulfite (Merck 106528) | | 2.5 g |
| Sodium thiosulfate (Merck 106516) | | 6.0 g |
| Aqua dest | | ad 1 liter |
| Adjust pH to 7.3 ± 0.2, autoclave for 15 min at 121° C. and after cooling add in sterile filtered condition: | | |
| Yeast extract (Marcor, 10 g yeast extract stirred cold into 100 ml VE-water and sterile-filtered) | | 2.5 ml |
| Phosphate buffer pH 7.3 | 1 molar solution | 20 ml |
| MOPS buffer pH 7.3 | 4 molar solution | 6 ml |
| (Sigma M1254, morpholinopropane sulfonic acid) (first add MOPS, thereafter phosphate slowly) | | |
| L-ascorbic acid (Na-salt Sigma A7631, 1 g in 2 ml VE-water | | 0.5 ml |
| Cast in agar strips for air-borne germ collecting apparatus and subject to γ-sterilisation (dose 16-25 kgray). | | |

Example 3

Microbial Content Test Agar

Difco without additives

Example 4

Soy Bean Casein Digest Agar

Difco with 1% (10 g/L) additional sodium pyruvate

Example 5

D/E-Agar

Difco without additives.

All five kinds of agar, for testing their capacity for the neutralisation of $H_2O_2$, are subjected to the action of 100 microliters of $H_2O_2$-bearing solutions with 10 ppm of 0.02% $H_2O_2$, 0.5% $H_2O_2$, 1% $H_2O_2$ and 2% (20,000 ppm) $H_2O_2$. Thereafter the level of $H_2O_2$ concentration on the agar surface is measured with peroxide test strips (Merck) (Table 1). While the agar according to the invention still neutralises 2% (20,000 ppm) $H_2O_2$, the basic medium MCT alone is not capable of completely neutralising 10 ppm. Kinds of agar which are known from the literature (Examples 4 and 5) can already no longer completely neutralise 0.5% $H_2O_2$.

After exposure with $H_2O_2$ with inoculation of *Staphylococcus aureus* ATCC 6538 with 10-100 colony-forming units the possible growth after $H_2O_2$ exposure is investigated (Table 2).

The agar additives according to the invention as set forth in Examples 1 and 2 permit germ growth even after exposure with high $H_2O_2$ amounts while the basic agar used already exhibits marked restraints upon growth, due to 10 ppm $H_2O_2$. The variants which are known in the literature with pyruvate additive alone or D/E-agar in known form neutralise rather more $H_2O_2$ but they also already exhibit very marked growth restraints from 0.5% $H_2O_2$.

TABLE 1

$H_2O_2$ concentration in the agar after application of 100 microliters of $H_2O_2$ solutions

| Concentration of the applied $H_2O_2$ solution | Agar Example 1 (invention) | Agar Example 2 (invention) | MCT agar Example 3 (standard comparison) | Soybean casein digest with 1% pyruvate Example 4 (literature) | D/E agar Example 5 (comparison) |
|---|---|---|---|---|---|
| 10 ppm | 0 ppm | 0 ppm | 1-2 ppm | 0 ppm | 0 ppm |
| 0.02% | 0 ppm | 0 ppm | 30 ppm | 0 ppm | 0 ppm |
| 0.5% | 0 ppm | 0 ppm | >100 ppm | 2-5 ppm | 2-5 ppm |
| 1.0% | 0 ppm | 0 ppm | >100 ppm | 5-10 ppm | 10 ppm |
| 2.0% (=20000 ppm) | 0 ppm | 0 ppm | | 20-30 ppm | 30 ppm |

TABLE 2

Growth of *Staph. aureus* 6538 after $H_2O_2$ exposure - inoculum of 10-100 colony-forming units (CFU) per agar surface (Petri dish agar strip contact slide)

| Concentration of the applied $H_2O_2$ solution | Agar Example 1 (invention) | Agar Example 2 (invention) | MCT agar Example 3 (standard comparison) | Soybean casein digest with 1% pyruvate Example 4 (literature) | D/E agar Example 5 (comparison) |
|---|---|---|---|---|---|
| 0 = control | 68 CFU | 73 CFU | 61 CFU | 71 CFU | 62 CFU |
| 10 ppm | 63 CFU | 74 CFU | 18 CFU | 68 CFU | 73 CFU |
| 0.02% | 71 CFU | 64 CFU | 0 CFU | 62 CFU | 65 CFU |
| 0.5% | 61 CFU | 59 CFU | 0 CFU | 12 CFU | 14 CFU |
| 1.0% | 65 CFU | 67 CFU | 0 CFU | 0 CFU | 0 CFU |
| 2.0% (=20000 ppm) | 69 CFU | 62 CFU | 0 CFU | 0 CFU | 0 CFU |

All 5 kinds of agar are cast in agar strips for RCS Highflow air-borne germ collecting apparatuses.

Thereafter in each case air samples were collected in parallel in an isolator with a comparatively high $H_2O_2$ residual loading and in an isolator ventilated overnight with a low $H_2O_2$ residual loading. For comparison purposes in each case non-loaded air was collected from a clean bench in a clean room. Inoculation with an inoculum of 10-100 colony-forming units of *Staph. aureus* ATCC 6538 was effected in each case directly after the air-borne germ collection procedure in order to anticipate a possible reduction in the $H_2O_2$ collected in the agar upon being left to stand. In that way the $H_2O_2$ loading should correspond to that which is found with a possible air-borne germ directly at the collection procedure. It will be seen from Table 3 that a normal standard agar permits germ growth after exposure with normal air without $H_2O_2$, but no longer in $H_2O_2$-loaded air, irrespective of the concentration. The agar types 4 and 5 known from the literature already exhibit marked weaknesses in performance in the isolator 1 at a relatively high level of $H_2O_2$ residual concentration while the agar types in accordance with the invention as set forth in Examples 1 and 2, as was to be expected from the results from Table 1, neutralise even relatively high levels of $H_2O_2$ concentration and permit unrestrained growth. The results are summarised in Table 3.

TABLE 3

Air-borne germ measurements in the isolator. 1000 L $H_2O_2$-bearing isolator air is collected with an RCS air-borne germ collector and the strips thereafter inoculated with *S. aureus* 6538. Comparison non-loaded clean bench air.

| Agar type | 1000 L air isolator 1 high $H_2O_2$ residual concentration | 1000 L air isolator 2 low $H_2O_2$ residual concentration | 1000 L clean bench air without $H_2O_2$ residual concentration |
|---|---|---|---|
| Agar Example 1 (invention) | 86 | 92 | 83 |
| Agar Example 2 (invention) | 81 | 79 | 88 |
| MCT agar Example 3 (standard comparison) | 0 | 0 | 91 |
| Soybean casein digest with 1% pyruvate Example 4 (literature) | 11 | 74 | 83 |
| D/E-agar Example 5 (comparison) | 7 | 92 | 94 |

Implementation of an application of $H_2O_2$-loaded surfaces in the isolator in dependence on the storage time of the agar used clearly shows in Table 4 the substantially better level of stability of the nutritive properties of the medium according to the invention as set forth in Example 1 in comparison with the D/E-standard agar known from the literature. With standard MCT agar the nutritive properties are admittedly more stable, but at a somewhat lower level in relation to *Staph. aureus*. In the case of the anaerobic germ *C. sporogenes* it will be seen that the lack of $H_2O_2$-neutralisation of MCT agar prevents the growth of anaerobes after $H_2O_2$ exposure while that is still readily possible with the agar according to the invention. In the case of anaerobic germs incubation is always anaerobic after inoculation.

The incubation temperature for all bacteria is adjusted in accordance with USP at 32.5° C. ±2.5° C.

TABLE 4

Growth of *S. aureus* 6538 and *C. sporogenes* after application of $H_2O_2$-fumigated isolator surfaces

| Agar type age 4 wks | Growth of | | Agar type age 3 mon | Growth of | | Agar type age 6 mon | Growth of | |
|---|---|---|---|---|---|---|---|---|
| | *S. aureus* | *C. sporogenes* | | *S. aureus* | *C. sporogenes* | | *S. aureus* | *C. sporogenes* |
| Agar Ex 1 (Inv) | 71 | 68 | Agar Ex 1 (Inv) | 88 | 92 | Agar Ex 1 (Inv) | 69 | 98 |
| MCT agar Ex 3 (standard comparison) | 58 | 0 | MCT agar Ex 3 (standard comparison) | 49 | 0 | MCT agar Ex 3 (standard comparison) | 52 | 0 |
| D/E-agar Ex 5 (comparison) | 68 | 16 | D/E-agar Ex 5 (comparison) | 23 | 0 | D/E- agar Ex 5 (comparison) | 0 | 0 |

Table 5 summarises the result of growth of an entire germ spectrum after passing through 1000 liters of $H_2O_2$-bearing isolator air in comparison in each case with 1000 liters of air from a clean bench without isolator. The growth of gram-positive cocci (*S. aureus*), gram-positive sporogenic rods (*B. subtilis*), anaerobic sporogenes (*C. sporogenes*), gram-negative enterobacteriaceae (*E. coli*), gram-negative non-fermenters (*P. aeruginosa*), yeasts (*C. albicans*) and fungi (*A. niger*) is investigated. On MCT agar and agar according to the invention all germs grow equally well after exposure with normal air (clean bench air). After exposure of $H_2O_2$-bearing isolated air all germs grow in a comparable number on the agar according to the invention as set forth in Example 2, while on MCT agar after exposure with $H_2O_2$-bearing isolator air no growth whatsoever can be found with all germs.

TABLE 5

Growth after collecting $H_2O_2$-bearing isolator air and clean bench air without $H_2O_2$ respectively

| Germ | Agar Example 2 1000 L isolator air | MCT agar Example 3 | Agar Example 1 | MCT agar Example 3 1000 L clean bench air |
|---|---|---|---|---|
| S. aureus | 85 | 0 | 82 | 76 |
| E. coli | 43 | 0 | 38 | 41 |
| P. aerunginosa | 61 | 0 | 56 | 58 |
| B. subtilis | 28 | 0 | 23 | 26 |
| C. sporogenes | 24 | 0 | 19 | 21 |
| C. albicans | 16 | 0 | 1 | 18 |
| A. niger | 38 | 0 | 42 | 36 |

The culture media according to the invention can be gamma-sterilised without problems.

It will be appreciated that the above-described Examples have been set forth by way of illustration of the present invention and that various modifications may be made therein without thereby departing from the spirit and scope of the invention.

What is claimed is:

1. A hydrogen-peroxide neutralizing gamma-sterilisable nutrient medium comprising casein soy peptone agar with between 2 and 10% by weight of sodium thioglycolate, between 10 and 30% by weight of sodium thiosulfate and between 5 and 20% by weight of sodium disulfite in each case with respect to the agar.

2. A nutrient medium as set forth in claim 1, further comprising between 0.1 and 0.25% by weight of sodium pyruvate with respect to the agar.

3. A nutrient medium as set forth in claim 1, further comprising at least one of bromocresol purple and bromocresol violet as a pH-indicator and between 10 and 50% by weight of polyvinylpyrrolidone with respect to the agar.

4. A nutrient medium as set forth in claim 1 comprising bromothymol blue as a pH-indicator and between 10 and 50% by weight of polyvinylpyrrolidone with respect to the agar.

5. A nutrient medium as set forth in claim 1, further comprising a buffer where between 20 and 50% of the total amount of buffer is morpholinopropane sulfonic acid and between 50 and 80% of the total amount of buffer is phosphate buffer.

6. A nutrient medium as set forth in claim 1, wherein the agar is microbial content test agar.

7. A nutrient medium as set forth in claim 1, further comprising at least one compound selected from the group consisting of betaine, glycine, cystine, proline and asparagine.

8. A nutrient medium as set forth in claim 1, further comprising between 0.05 and 0.25% by weight of sodium pyruvate with respect to the agar.

9. A nutrient medium as set forth in claim 3, wherein the content of polyvinylpyrrolidone with respect to the agar is between 30 and 45% by weight.

10. A nutrient medium as set forth in claim 4, wherein the content of polyvinylpyrrolidone with respect to the agar is between 30 and 45% by weight.

11. A method for detecting microorganisms in hydrogen peroxide-bearing air or on a hydrogen peroxide-bearing surface, said method comprising contacting said air or surface with a nutrient medium as set forth in claim 1, and detecting growth of microorganisms in said medium.

12. A hydrogen-peroxide neutralizing nutrient medium sterilized by gamma radiation comprising casein soy peptone agar, between 2 and 10% by weight of sodium thioglycolate, between 10 and 30% by weight of sodium thiosulfate and between 5 and 20% by weight of sodium disulfite in each case with respect to the agar.

13. A nutrient medium as set forth in claim 12, further comprising between 0.1 and 0.25% by weight of sodium pyruvate with respect to the agar.

14. A nutrient medium as set forth in claim 12, further comprising at least one of bromocresol purple and bromocresol violet as a pH-indicator and between 10 and 50% by weight of polyvinylpyrrolidone with respect to the agar.

15. A nutrient medium as set forth in claim 12 comprising bromothymol blue as a pH-indicator and between 10 and 50% by weight of polyvinylpyrrolidone with respect to the agar.

16. A nutrient medium as set forth in claim 12, further comprising a buffer where between 20 and 50% of the total amount of buffer is morpholinopropane sulfonic acid and between 50 and 80% of the total amount of buffer is phosphate buffer.

17. A nutrient medium as set forth in claim 12, wherein the agar is microbial content test agar.

18. A nutrient medium as set forth in claim 12, further comprising at least one compound selected from the group consisting of betaine, glycine, cystine, proline and asparagine.

19. A method for detecting microorganisms in hydrogen peroxide-bearing air, said method comprising contacting said air with a nutrient medium as set forth in claim 12, and detecting growth of microorganisms in said medium.

20. A method for detecting microorganisms on a hydrogen peroxide-bearing surface comprising contacting said surface with a nutrient medium as set forth in claim 12, and detecting growth of microorganisms in said medium.

21. A nutrient medium as set forth in claim 12, further comprising between 0.05 and 0.25% by weight of sodium pyruvate with respect to the agar.

22. A nutrient medium as set forth in claim 14, wherein the content of polyvinylpyrrolidone with respect to the agar is between 30 and 45% by weight.

23. A nutrient medium as set forth in claim 15, wherein the content of polyvinylpyrrolidone with respect to the agar is between 30 and 45% by weight.

* * * * *